United States Patent
Fujii et al.

(10) Patent No.: US 10,632,057 B2
(45) Date of Patent: Apr. 28, 2020

(54) COSMETIC COMPOSITION FOR EYES

(71) Applicant: SHISEIDO COMPANY, LTD., Tokyo (JP)

(72) Inventors: Koichi Fujii, Kanagawa (JP); Kiriko Chiba, Kanagawa (JP); Hisae Watanabe, Kanagawa (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 0 days.

(21) Appl. No.: 16/307,003

(22) PCT Filed: May 29, 2017

(86) PCT No.: PCT/JP2017/019956
§ 371 (c)(1),
(2) Date: Dec. 4, 2018

(87) PCT Pub. No.: WO2017/212974
PCT Pub. Date: Dec. 14, 2017

(65) Prior Publication Data
US 2019/0216711 A1    Jul. 18, 2019

(30) Foreign Application Priority Data
Jun. 8, 2016 (JP) .................. 2016-114017

(51) Int. Cl.
*A61K 8/73* (2006.01)
*A61Q 1/10* (2006.01)
*A61K 8/898* (2006.01)
*A61K 8/891* (2006.01)
*A61K 8/19* (2006.01)
*A61K 8/92* (2006.01)
*A61K 8/58* (2006.01)

(52) U.S. Cl.
CPC ............... *A61K 8/732* (2013.01); *A61K 8/19* (2013.01); *A61K 8/585* (2013.01); *A61K 8/891* (2013.01); *A61K 8/898* (2013.01); *A61K 8/92* (2013.01); *A61Q 1/10* (2013.01)

(58) Field of Classification Search
CPC .......... A61K 8/19; A61K 8/585; A61K 8/732; A61K 8/891; A61K 8/192; A61Q 1/10
See application file for complete search history.

(56) References Cited

U.S. PATENT DOCUMENTS

| 2007/0196306 A1 | 8/2007 | Lezer et al. |
| 2013/0287824 A1 | 10/2013 | Inaba |
| 2016/0081904 A1* | 3/2016 | Konishi ................ A61K 8/26 424/70.122 |
| 2017/0224608 A1 | 8/2017 | Fujiyama et al. |

FOREIGN PATENT DOCUMENTS

| EP | 2236128 A1 | 10/2010 |
| EP | 3175841 | 6/2017 |
| JP | 444815 | 4/1992 |
| JP | 1029910 A2 | 2/1998 |
| JP | 2004238363 A2 | 8/2004 |
| JP | 2006306854 | 11/2006 |
| JP | 2007314655 A2 | 12/2007 |
| JP | 2010132619 | 6/2010 |
| JP | 2011207865 A2 | 10/2011 |
| JP | 2013107827 A2 | 6/2013 |
| JP | 2013227246 A2 | 11/2013 |
| JP | 201437397 | 2/2014 |
| JP | 5766981 B2 | 8/2015 |
| WO | 2016/017624 A1 | 2/2016 |

OTHER PUBLICATIONS

Mizudori Yoichi et al. (JP 2004300092 A, using the Eng. Trans). Oct. 28, 2004, 18 pages.*
International Search Report (ISR) dated Sep. 12, 2017 filed in PCT/JP2017/019956.
International Search Opinion (PCT/ISA/237) dated Sep. 12, 2017 filed in PCT/JP2017/019956 and its partial English translation.
Extended European Search Report (EESR) dated Jan. 23, 2020 issued in the corresponding European patent Application No. 17810153.1.

* cited by examiner

*Primary Examiner* — Blessing M Fubara
(74) *Attorney, Agent, or Firm* — Rankin, Hill & Clark LLP

(57) ABSTRACT

A cosmetic composition for the eyes of the present disclosure contains 10.01 to 30% by mass of a silicone series film forming agent and 25 to 70% by mass of a volatile oil component with respect to the total amount of the cosmetic composition for the eyes. The amount of a volatile silicone series oil component is 25% by mass or greater with respect to the total volatile oil component, and the hardness is 30 or greater and 100 or less. The cosmetic composition has superior cosmetic lasting effects and can be utilized as both mascara and eyeliner.

9 Claims, No Drawings

COSMETIC COMPOSITION FOR EYES

CROSS REFERENCE TO RELATED APPLICATIONS

The present application is a National Phase Entry of PCT International Application No. PCT/JP2017/019956 filed on May 29, 2017, claiming priority to Japanese Patent Application No. 2016-114017 filed on Jun. 8, 2016. The contents of the applications are incorporated herein by reference in its entirety.

TECHNICAL FIELD

The present disclosure is related to a cosmetic composition for the eyes.

BACKGROUND ART

Conventionally, mascara, eyeliner, eyebrow pencils, etc. are known as eye cosmetics. Mascara is a cosmetic for the eyes that can enhance the impression of the eyes by making the eyelashes thick, long, and curled, and eyeliner is a cosmetic for the eyes that enhances the impression of the eyes by being applied to draw a line at the edges of eyelids, thereby emphasizing the outline of the eyes and causing them to appear larger.

A certain degree of strength is required for the cosmetic film of mascara because superior long lasting effects are necessary for the curling effect to be prevented from decreasing over time and such that makeup will not be transferred to the lower eyelid over time due to blinking. On the other hand, since the target portion of use of eyeliner is a narrow range limited to the edges of the eyes, a supple cosmetic film is desired such that it spreads smoothly when used, is applied easily and has superior utilization properties, and such that the cosmetic film does not partially become unapplied due to motions such as blinking. In this manner, because the functions which are desired of mascara and eyeliner are different, cosmetics which are dedicated to each use are conventionally provided.

Meanwhile, there are consumer needs that desire application with only one item because mascara and eyeliner are applied to the eyes and eyebrows, which are adjacent to each other, or desire avoiding having to carry mascara and eyeliner constantly to fix makeup. From this point of view, whether a cosmetic that can be used both as mascara and eyeliner can be produced has been being considered. For example, Japanese Patent No. 5766981 discloses a mascara/eyeliner cosmetic composition which can be used as both mascara and eyeliner.

SUMMARY

Technical Problem

The cosmetic composition that combines mascara and eyeliner disclosed in Patent Document 1 attempts to have a curl maintaining effect, a volume increasing effect, and sustainability of cosmetic effect which are desired of mascara, as well as smoothness at the time of application and a supple cosmetic film, which are desired of eyeliner. However, there is a problem that the cosmetic lasting properties thereof are extremely poor. In order to improve cosmetic lasting properties, it is necessary to increase the amount of a film forming agent. However, if the amount of film forming agent is increased, a hard decorative film cannot follow the movement of the eyelid when utilized as eyeliner, and the cosmetic becomes partially unapplied. When utilized as mascara, the cosmetic film is excessively supple, the curl maintaining effect and the volume increasing effect are lowered, and the cosmetic effect is weakened.

The present disclosure has been developed in view of the foregoing circumstances. The present disclosure provides a cosmetic composition for the eyes which has superior cosmetic lasting effects and can be utilized as both mascara and eyeliner.

A cosmetic composition for the eyes of the present disclosure contains 10.01 to 30% by mass of a silicone series film forming agent and 25 to 70% by mass of a volatile oil component with respect to the total amount of the cosmetic composition for the eyes. The amount of a volatile silicone oil component is 25% by mass or greater with respect to the total volatile oil component, and the hardness is 30 or greater and 100 or less.

It is preferable for the silicone series film forming agent to be trimethylsiloxysilicic acid or siliconized pullulan.

It is preferable for the siliconized pullulan to be tri(trimethylsiloxy) silylpropylcarbamic acid pullulan.

It is preferable for the volatile silicone series oil component to be a volatile straight chain silicone series oil component.

It is preferable for the cosmetic composition for the eyes according to the present disclosure to further contain 0.01 to 20% by mass of a solid oil component.

It is preferable for the cosmetic composition for the eyes according to the present disclosure to further contain purified water in an amount within a range from 0.01 to 5% by mass.

The cosmetic composition for the eyes of the present disclosure may further comprise red iron oxide.

The cosmetic composition for the eyes of the present disclosure may be mascara.

The cosmetic composition for the eyes of the present disclosure may also be employed as both mascara and eyeliner.

The cosmetic composition for the eye of the present disclosure contains 10.01 to 30% by mass of a silicone type film forming agent and 25 to 70% by mass of a volatile oil component with respect to the total amount of the cosmetic composition for the eyes, a volatile silicone oil component is 25% by mass or greater with respect to the total volatile oil component, and the hardness is 30 or greater and 100 or less. Therefore, the cosmetic lasting effect is superior, and the cosmetic composition for the eyes can be used both as mascara and eyeliner.

DESCRIPTION OF EMBODIMENTS

Hereinafter, the cosmetic composition for the eyes of the present disclosure will be described in detail.

The cosmetic composition for the eye of the present disclosure contains 10.01 to 30% by mass of a silicone type film forming agent and 25 to 70% by mass of a volatile oil component with respect to the total amount of the cosmetic composition for the eyes, a volatile silicone oil component is 25% by mass or greater with respect to the total volatile oil component, and the hardness is 30 or greater and 100 or less.

Each of the components will be described in detail below.

[Silicone Series Film Forming Agent]

The film forming agent of the cosmetic composition for the eyes of the present disclosure is a silicone series film forming agent. Preferable examples of the silicone series film forming agent include trimethylsiloxysilicic acid, siliconized pullulan, (acrylates/dimethicone) copolymer, silsesquioxane series, etc. Trimethylsiloxysilicic acid and siliconized pullulan are preferable from the viewpoints of cosmetic lasting effects, etc.

These silicone series film forming agents may be used alone or in appropriate combinations of two or more.

The trimethylsiloxysilicic acid preferably has a weight average molecular weight of 10000 or more. By having a weight-average molecular weight of 10,000 or more, it is possible to further impart cosmetic lasting effects on eyelashes and the edges of eyes.

The weight average molecular weight is a polystyrene converted value as measured by gel permeation chromatography (GPC).

A trimethylsiloxysilicic acid which is prepared by a known production method may be employed.

Further, examples of commercially available products include X-21-5250 (50% decamethyl cyclopentasiloxane solution by Shin Etsu Chemical Industries), X-21-5250 L (50% dimethicone solution by Shin Etsu Chemical Industries), X-21-5616 (60% isododecane solution by Shin Etsu Chemical Industries), X-21-5249 (50% decamethyl cyclopentasiloxane solution by Shin Etsu Chemical Industries), X-21-5249 L (50% dimethicone solution by Shin Etsu Chemical Industries), KF 7312 (50% decamethyl cyclopentasiloxane solution by Shin Etsu Chemical Industries), KF-7312 K (60% dimethicone solution by Shin Etsu Chemical Industries), KF 7312 L (50% dimethicone solution by Shin Etsu Chemical Industries), KF-7312 T (60% methyl trimethicone solution by Shin Etsu Chemical Industries), X-21-5595 (60% isododecane solution by Shin Etsu Chemical Industries), KF-9021 (50% decamethyl cyclopentasiloxane solution by Shin Etsu Chemical Industries), KF-9021 L (50% dimethicone solution by Shin Etsu Chemical Industries), MQ-1600 Solid Resin (by Toray Dow Silicone, 100% pure), Wacker-Belsil TMS 803 (by Asahi Kasei Wacker Silicone Co., Ltd., 100% pure), etc.

In siliconized pullulan, the bonding ratio of the silicone compound to the reactive functional group of the pullulan varies depending on the type thereof, but in general, the average number of bonds (degree of substitution) of the silicone compound per unit sugar constituting the polysaccharide compound is favorably within a range from 0.5 to 3.0. Moreover, in the present disclosure, the degree of substitution is calculated from the Si content (% by mass) within the compound.

Note that when siliconized pullulan is blended, if it is dissolved in low molecular weight silicone oil or light isoparaffin and blended, ease of blending and a sensation of use can be improved.

It is preferable for the siliconized pullulan to be tri (trimethylsiloxy) silylpropylcarbamic acid pullulan.

A siliconized pullulan which is prepared by a known production method may be employed (the method disclosed in Japanese Unexamined Patent Publication No. H10-29910, for example).

In addition, examples of commercially available products include TSPL-30-ID (tri (trimethylsiloxy) silylpropylcarbamate pullulan, 30% isododecane solution by Shin Etsu Chemical Industries), and TSPL-30-D5 (tri (trimethylsiloxy) silyl Propyl carbamate pullulan, 30% decamethyl cyclopentasiloxane solution by Shin Etsu Chemical Industries).

The silicone series film forming agent is contained in an amount within a range from 10.01 to 30% by mass and more preferably a range from 12 to 28% by mass, with respect to the total amount of the cosmetic composition for the eyes.

By the content of the silicone type film forming agent being 10.01% by mass or greater and 30% by mass or less, the cosmetic lasting effect is improved. When used as mascara, the curl maintaining effect is high, clumping becomes less likely to occur, and the cosmetic effect is remarkably improved. When used as eyeliner, the cosmetic composition for the eyes follows the movement of the eyelids in a supple manner, and bleeding becomes less likely to occur.

[Volatile Oil Component]

(Volatile Silicone Series Oil Component)

The volatile silicone series oil component is a silicone oil having a boiling point of 250° C. or less at 1 atm (101.325 kPa). Volatile silicone series oils include volatile cyclic silicone series oils and volatile straight chain silicone series oils.

Examples of volatile cyclic silicone series oils may include dodecamethyl cyclohexasiloxane, decamethyl cyclopentasiloxane, octamethylcyclotetrasiloxane, etc. Examples of volatile straight chain silicone series oils may include low molecular weight straight chain dimethicone (0.65 cs, 1 cs, 1.5 cs, 2 cs, etc.), methyl trimethicone (TMF-1.5, etc.) which is a low molecular weight branched silicone, low molecular weight alkyl modified silicone, etc. Among these, volatile straight chain silicone series oils and low molecular weight branched silicones are preferred from the viewpoints of improving quick drying properties and preventing secondary adhesion immediately after application. Examples of volatile straight chain silicone series oils and low molecular weight branched silicones include low molecular weight methyl polysiloxanes (1 cS, 1.5 cS, 2 cS, etc.) such as decamethyl tetrasiloxane, octamethyl trisiloxane, decamethyl trisiloxane and dimethicone (dimethyl polysiloxane), as well as branched silicones such as methyl trimethicone (TMF-1.5).

The content of the volatile silicone series oil component is 25% by mass or greater, preferably 30% by mass or greater, and more preferably 50% by mass or greater with respect to the total amount of the volatile oil. If the volatile silicone series oil component is 25% by mass or greater with respect to the total amount of the volatile oil component, compatibility with the silicone series film forming agent is improved, surface quick drying properties becomes favorable, and the cosmetic lasting effect is improved. When utilized as a cosmetic for the eyes, particularly as mascara, the curl maintaining effect is high and the cosmetic effect is remarkably improved. When utilized as eyeliner, the cosmetic composition for the eyes follows movements of the eyelids in a supple manner, and bleeding will become less likely to occur.

(Volatile Oil Components Other than Volatile Silicone Series Oil)

A volatile hydrocarbon oil such as light isoparaffin is an example of a volatile oil component other than the volatile silicone series oil component, for example.

Commercially available products of light isoparaffin include Isopar H (by Esso Chemicals), isododecane (by Bayer), isohexadecane (by Uniqema), IP Solvent 1620 MU, IP Solvent 2028 MU, IP Solvent 2835 (by Idemitsu Kosan), etc.

It is desirable for the content of the volatile oil component other than the volatile silicone series oil to be 75% by mass or less, preferably 70% by mass or less, and more preferably 50% by mass or less with respect to the total amount of the volatile oil. If the content is 75% by mass or less, the cosmetic for the eyes can be applied easily and the utilization properties thereof can be improved.

The content of the volatile oil component is 25 to 70% by mass with respect to the total amount of the cosmetic composition for the eyes. By the cosmetic composition for the eyes including a volatile oil component in an amount of 25% by mass or greater, it is possible to improve the cosmetic lasting effect, to facilitate application, and to improve the utilization properties thereof. In addition, if the content of the volatile oil component is 70% by mass or less, it is possible to achieve appropriate surface quick drying properties.

(Nonvolatile Oil Component)

The cosmetic composition for the eyes of the present disclosure may contain a nonvolatile oil component. It is preferable for the content of the nonvolatile oil component to be within a range from 0 to 30% by mass and more preferably a range from 1 to 20% by mass with respect to the total amount of the cosmetic composition for the eyes. By setting the content of the nonvolatile oil component to 30% by mass or less, the hardness of the cosmetic composition for the eyes can be adjusted to an appropriate level.

Examples of nonvolatile oils include cyclic silicone oil, nonvolatile silicone oil, polar oil, nonpolar oil, solid oil, semisolid oil, etc.

Examples of cyclic silicone oils include cyclopentasiloxane, cyclohexane siloxane, octamethyl cyclotetrasiloxane, decamethyl cyclopentasiloxane, dodecamethyl cyclohexasiloxane, etc. Examples of nonvolatile silicone oils include methyl polysiloxane, high molecular weight dimethyl polysiloxane (for 6 cS, for example), etc.

Examples of polar oils include isopropyl myristate, octyl dodecyl myristate, isopropyl palmitate, butyl stearate, hexyl laurate, myristyl myristate, decyl oleate, hexyl decyl dimethyl octanoate, cetyl lactate, myristyl lactate, lanolin acetate, isocetyl stearate, isocetyl isostearate, cholesteryl 12-hydroxystearate, ethylene glycol di-2-ethylhexanoate, dipentaerythritol fatty acid ester, N-alkyl glycol monoisostearate, neopentyl glycol dicaprate, diisostearyl malate, glycerin di-2-heptylundecanoate, trimethylolpropane tri-2-ethylhexanoate, tetra-2-ethyhexanoic acid pentane erythritol, glycerin tri-2-ethylhexanoate, trimethylolpropane triisostearate, cetyl 2-ethylhexanoate, 2-ethylhexyl palmitate, glycerin trimyristate, glyceryl tri (caprylic/capric acid), triethylhexanoin, cetyl ethylhexanoate, polyglyceryl-2 triisostearate, dipentaerythrityl hexahydroxystearate, pentaerythrityl tetra (behenic acid/benzoic acid/ethylhexanoic acid), PPG-3 dipivalic acid, dipentaerythrityl tripolyhydroxystearate, pentaerythrityl tetra (ethylhexanoic acid/benzoic acid), macadamia nut oil polyglyceryl-6 esters behenate, dimer dilinoleic acid (phytosteryl/behenyl), lanolin, diethylhexyl succinate, lanolin octyldodecyl fatty acid, isostearyl palmitate, diheptylundecyl adipate, isocetyl myristate, dihexyldecyl adipate, diisopropyl sebacate, pentaerythrityl tetraethylhexanoate, glyceride tri-2-heptylundecanoate, methyl ester of castor oil fatty acid, oleyl oleate, cetostearyl alcohol, acetoglyceride, 2-heptylundecyl palmitate, diisobutyl adipate, 2-octyldodecyl N-lauroyl-L-glutamate, di-2-heptylundecyl adipate, ethyl laurate, Di-2-ethylhexyl sebacate, 2-hexyldecyl myristate, 2-hexyldecyl palmitate, 2-hexyldecyl adipate, diisopropyl sebacate, 2-ethylhexyl succinate, ethyl acetate, butyl acetate, amyl acetate, triethyl citrate, triglycerin, trioctanoate glycerin, triisopalmitate glycerol, tetra isostearate sucrose, hexa isostearate sucrose, etc.

Examples of nonpolar oils include hydrocarbon oils such as liquid paraffin, squalane, squalene, paraffin, isododecane, isohexadecane, hydrogenated polydecene, heavy liquid isoparaffin, etc.

It is preferable for the cosmetic composition for the eyes according to the present disclosure to contain a solid oil component. A solid oil component is a substance which is solid under ordinary temperature and normal pressure and has a melting point. Examples of solid oils include solid fats and oils such as cocoa butter, coconut oil, horse oil, hardened coconut oil, palm oil, beef tallow, sheep fat, and hydrogenated castor oil; hydrocarbons such as paraffin wax (linear hydrocarbon), microcrystalline wax (branched saturated hydrocarbons), ceresin wax, wolfberry wax, montan wax and Fischer-Tropsch wax; polar waxes such as sucrose acetate stearate, ethylene glycol fatty acid (C18 to C30) and ester; waxes such as beeswax, lanolin, carnauba wax, candelilla wax, rice bran wax (rice wax), gay wax, jojoba oil, nucca wax, montan wax, kapok wax, bayberry wax, shellac wax, sugar cane wax, isopropyl lanolin fatty acid, hexyl laurate, reduced lanolin, hard lanolin, POE (polyoxyethylene) lanolin alcohol ether, POE lanolin alcohol acetate, POE cholesterol ether, lanolin fatty acid polyethylene glycol, and POE hydrogenated lanolin alcohol ether; higher fatty acids such as myristic acid, palmitic acid, stearic acid, and behenic acid; higher alcohols such as cetyl alcohol, stearyl alcohol, behenyl alcohol, myristyl alcohol, and cetostearyl alcohol; silicone waxes such as (acrylates/stearyl acrylate/methacrylic acid dimethicone) copolymer, acrylates/behenyl acrylate/dimethicone methacrylate) copolymer, alkyl methicone, alkyl dimethicone, alkyl dimethyl silyl polypropyl silsesquioxane, stearoxy trimethyl silane, etc.

The content of the solid oil component is preferably within a range from 0.01 to 20% by mass, and more preferably a range from 5 to 15% by mass with respect to the total amount of the cosmetic composition for the eyes. The texture of the cosmetic composition for the eyes can be adjusted by adjusting the content of the solid oil content to 0.01% by mass or greater, or by setting it to 20% by mass or less. When the cosmetic composition for the eyes is utilized as mascara, a curling effect to eyelashes can be exhibited.

Examples of semi solid oils include vegetable fats such as petrolatum, lanolin, shea butter and partially hydrogenated coconut oil; partially hydrogenated jojoba oil, bisdiglyceryl polyacyl adipate-2, tetra (behenic acid/benzoic acid/ethylhexane acid) pentaerythrityl, macadamia nut oil polyglyceryl-6-esters behenate, dimer dilinoleic acid (phytosteryl/behenyl), hexaoxystearic acid dipentaerythritol, etc.

(Coloring Material)

A coloring material which is generally capable of being blended in cosmetics for the eyes can be used in the cosmetic composition for the eyes of the present disclosure.

Specific preferable examples include inorganic powders such as titanium oxide, zinc oxide, black iron oxide, yellow iron oxide, ultramarine blue, iron blue, talc, mica, sericite, kaolin, titanium mica, chromium oxide and chromium hydroxide.

In addition, it is possible to add red iron oxide to the cosmetic composition for the eyes of the present disclosure. It had been difficult to add red iron oxide to cosmetics due to a concern of aggregation when added to a conventional liquid eyeliner, due to color tone not matching even if the coloring material is of the same formulation due to the influence of a base material, and due to the influence of the texture of the base material appearing in the finish. By blending red iron oxide, it is easy to adjust the color tone, and it is possible to impart the impression of gentle eyes. In addition, by setting the colors of the mascara and the eyeliner to match, it is possible to unify the color of the eyelashes and the eyeline, imparting a sensation of unity to the eye, and it becomes possible to further enhance the cosmetic effect of making the eyes being emphasized.

The inorganic powder may be utilized untreated as is, but it is preferable for a hydrophobized powder obtained by subjecting the powder surface to hydrophobic treatment to be employed.

The hydrophobized powder can be obtained by mixing inorganic powder with silicones such as methyl hydrogen polysiloxane and dimethyl polysiloxane; dextrin fatty acid ester, higher fatty acid, higher alcohol, fatty acid ester, metal soap, alkyl phosphate ether, a fluorine compound, or hydrocarbons such as squalane, paraffin, etc., to subject the powder surface to hydrophobic treatment by a wet method that utilizes a solvent, a gas phase method, a mechanochemical method, etc.

The content of the coloring material is preferably 0.1% by mass or greater, and more preferably 3% by mass or greater with respect to the total amount of the cosmetic composition for the eyes. By the content of the coloring material being 0.1% by mass or greater, the sedimentation rate of the inorganic powder can be favorably maintained. Further, the content of the inorganic powder is preferably 30% by mass or less, more preferably 10% by mass or less, and still more preferably 7% by mass or less. There are cases in which the hardness will increase if the content of the inorganic powder is excessively high.

It is preferable for the cosmetic composition for the eyes of the present disclosure to contain purified water. It is preferable for the content of the purified water to be within a range from 0.01 to 5% by mass, and more preferably a range from 1.5 to 2.5% by mass with respect to the total amount of the cosmetic composition for the eyes. The texture of the cosmetic composition for the eyes can be adjusted and made smooth by adjusting the content of the purified water to 0.01% by mass or greater, or by setting it to 5% by mass or less. In addition, when a small amount (0.01 to 5% by mass) of purified water is contained in this manner, water is dispersed in the cosmetic composition for the eyes to improve the utilization properties thereof. Particularly in the case that the cosmetic composition for the eyes is oily mascara, it is possible to remarkably improve the cosmetic lasting effect compared to conventional emulsified mascara.

Various components which are generally blended in cosmetic compositions for the eyes may be blended in the cosmetic composition for the eyes of the present disclosure, within a range that does not adversely affect the effects thereof. Specific examples of such components may include other powders, resins, or oils, fibers, pharmaceutical agents, emulsifying agents, thickeners, clay minerals, antiseptics, antifoaming agents, moisturizers, alcohols, polyhydric alcohols, water soluble polymers, pharmaceutical agents, antioxidants, ultraviolet ray absorbing agents, ultraviolet ray scattering agents, other film forming agents, fragrances, etc.

EXAMPLES

Hereinafter, the present disclosure will be described in greater detail with reference to Examples. However, the present disclosure is not limited to these Examples. Moreover, in the following examples and the like, the content of each component is indicated as % by mass unless otherwise noted.

Cosmetic compositions for the eyes having the compositions listed in Table 1 below were prepared by a conventional method. Moreover, X-21-5595 (60% isododecane solution by Shin Etsu Chemical Industries) was employed as the trimethylsiloxysilicic acid as a film forming agent, and TSPL-30-ID (30% isododecane solution by Shin Etsu Chemical Industries) was employed as the tri (trimethylsiloxy) silylpropyl carbamate pullulan.

The hardness of the cosmetic composition for the eyes was measured in the following manner.
(Hardness)
The cosmetic compositions for the eyes prepared as Examples and Comparative Examples were left for 4 weeks at 25° C. and 60% RH. 8 mm φ containers were filled with approximately 45 grams of the left samples and loaded into BV skin cream (glass bottles by Japan Seiko Glass), and the surfaces of the samples were flattened. Next, a Sun rheometer: (CMPAC-II by Sun Science) was employed to measure the hardness with an 8 mm φ disk needle, a needle penetration depth of 10 mm, a penetration speed of 300 mm/min, and a 2K range reading. The measurement temperature was 30° C.
(Evaluation)
(Cosmetic Lasting Effect)
Practical use tests were conducted by panelists (10 people) for samples of the Examples and Comparative Examples. Each composition was scored with respect to the cosmetic lasting effects thereof based on the scores below. Averages of the scores for each composition were calculated, and the calculated average scores were designated as evaluation values, and the cosmetic lasting effects were evaluated according to the evaluation criteria below.
(Scores)
5 points: Very Good
4 points: Good
3 points: Fair
2 points: Poor
1 point: Very Poor
(Evaluation Criteria)
A: Evaluation value (average value) of 4.0 or more and 5.0 or less
B: Evaluation value (average value) of 2.5 or more and 4.0 or less
C: Evaluation value (average value) of 1.0 or more and 2.5 or less
The evaluation results are shown in Table 1 together with the composition blends.

TABLE 1

| | Component | Example 1 | Example 2 | Example 3 | Example 4 |
|---|---|---|---|---|---|
| Volatile Hydrocarbon Oil Component | light isoparaffin | Remainder | Remainder | Remainder | Remainder |
| Volatile Silicone Series Oil Component | decamethyl trisiloxane methyl trimethicone | 25 | 25 | 20 | 15 |
| Non Volatile Silicone Series Oil Component | methyl polysiloxane | 2 | 2 | 2 | 2 |
| Non Volatile Polar Oil Component | sucrose tetraisostearate | 1 | 1 | 1 | 1 |
| Semisolid Oil Component | dipentaerythritol hexaoxystearate | — | — | — | — |
| Wax | paraffin | 4.2 | 4.2 | 4.2 | 4.2 |
| | microcrystalline wax | 0.3 | 0.3 | 0.3 | 0.3 |

TABLE 1-continued

| | Component | | | | |
|---|---|---|---|---|---|
| | sucrose acetate stearate | 3 | 3 | 3 | 3 |
| | candellila wax | 1.5 | 1.5 | 1.5 | 1.5 |
| Activating Agent | polyoxyethylene methylpolysilioxane copolymer | 2 | 2 | 2 | 2 |
| | polyoxyethylene hardened castor oil triisostearate (20 E.O.) | 1 | 1 | 1 | 1 |
| Gelling Agent | dextrin palmitate | 9 | 9 | 9 | 9 |
| | (palmitic acid/2-ethylhexanoic acid) dextrin | 1 | 1 | 1 | 1 |
| Film Forming Agent | trimethyl siloxysilicate | 12 | 12 | 12 | 12 |
| | 3-[tris (trimethylsiloxy) silyl] propylcarbamic acid pullulan | 0.9 | 0.9 | 0.9 | 0.9 |
| Thickener | dimethyldistearyl ammonium hectorite | 6 | 6 | 6 | 6 |
| Coloring Material | black iron oxide | 5 | 3 | 5 | 5 |
| | yellow iron oxide | — | 0.9 | — | — |
| | red iron oxide | — | 1 | — | — |
| Coloring Material Surface Treating Agent | n-octyl triethoxysilane | 0.1 | 0.1 | 0.1 | 0.1 |
| Powder | methyl siloxane network polymer | 3 | 3 | 3 | 3 |
| Water | water | 1.8 | 1.8 | 1.8 | 1.8 |
| Moisturizer | 1,3-butyrene glycol | 1.8 | 1.8 | 1.8 | 1.8 |
| Antioxidant | d-δ-tocopherol | 0.05 | 0.05 | 0.05 | 0.05 |
| | BHT | 0.05 | 0.05 | 0.05 | 0.05 |
| Fragrance | Fragrance | 0.05 | 0.05 | 0.05 | 0.05 |
| | Total | 100 | 100 | 100 | 100 |
| Film Forming Agent | Blended Amounts | 12.9 | 12.9 | 12.9 | 12.9 |
| Volatile Oil Component | Volatile Silicone Series Oil Component Content | 25 | 25 | 20 | 15 |
| | Volatile Hydrocarbon Oil Component Content | 19.25 | 19.35 | 24.25 | 29.25 |
| | Total Amount of Volatile Oil Component | 44.25 | 44.35 | 44.25 | 44.25 |
| | Volatile Silicone Series Oil Component/Total Volatile Oil Component | 0.56 | 0.56 | 0.45 | 0.34 |
| Physical Property Values | Hardness (after 4 weeks) | 81 | 80 | 81 | 93 |
| Evaluation | Practical Use Test (Cosmetic Lasting Effect) | A | B | B | B |

| | Component | Example 5 | Comparative Example 1 | Comparative Example 2 |
|---|---|---|---|---|
| Volatile Hydrocarbon Oil Component | light isoparaffin | Remainder | Remainder | Remainder |
| Volatile Silicone Series Oil Component | decamethyl trisiloxane | 7 | | 10 |
| | methyl trimethicone | 7 | | |
| Non Volatile Silicone Series Oil Component | methyl polysiloxane | 2 | 2 | 2 |
| Non Volatile Polar Oil Component | sucrose tetraisostearate | 1 | 1.2 | 1 |
| Semisolid Oil Component | dipentaerythritol hexaoxystearate | — | 3 | — |
| Wax | paraffin | 4.2 | 4.2 | 4.2 |
| | microcrystalline wax | 0.3 | 0.3 | 0.3 |
| | sucrose acetate stearate | 3 | 3 | 3 |
| | candellila wax | 1.5 | 1.5 | 1.5 |
| Activating Agent | polyoxyethylene methylpolysilioxane copolymer | 2 | 2 | 2 |
| | polyoxyethylene hardened castor oil triisostearate (20 E.O.) | 1 | 1 | 1 |
| Gelling Agent | dextrin palmitate | 9 | 7 | 9 |
| | (palmitic acid/2-ethylhexanoic acid) dextrin | 1 | 1 | 1 |
| Film Forming Agent | trimethyl siloxysilicate | 10.02 | 12 | 10.02 |
| | 3-[tris (trimethylsiloxy) silyl] propylcarbamic acid pullulan | 0.9 | 0.9 | 0.9 |
| Thickener | dimethyldistearyl ammonium hectorite | 6 | 5 | 6 |
| Coloring Material | black iron oxide | 5 | 5 | 5 |
| | yellow iron oxide | — | — | — |
| | red iron oxide | — | — | — |
| Coloring Material Surface Treating Agent | n-octyl triethoxysilane | 0.1 | 0.1 | 0.1 |
| Powder | methyl siloxane network polymer | 3 | — | 3 |
| Water | water | 1.8 | 1.5 | 1.8 |
| Moisturizer | 1,3-butyrene glycol | 1.8 | 1.5 | 1.8 |
| Antioxidant | d-δ-tocopherol | 0.05 | 0.05 | 0.05 |
| | BHT | 0.05 | 0.05 | 0.05 |
| Fragrance | Fragrance | 0.05 | 0.05 | 0.05 |
| | Total | 100 | 100 | 100 |
| Film Forming Agent | Blended Amounts | 10.92 | 12.9 | 10.92 |
| Volatile Oil Component | Volatile Silicone Series Oil Component Content | 14 | 0 | 10 |
| | Volatile Hydrocarbon Oil Component Content | 32.23 | 44.65 | 36.23 |
| | Total Amount of Volatile Oil Component | 46.23 | 44.65 | 46.23 |
| | Volatile Silicone Series Oil Component/Total Volatile Oil Component | 0.30 | 0.00 | 0.22 |
| Physical Property Values | Hardness (after 4 weeks) | 57 | 37 | 62 |
| Evaluation | Practical Use Test (Cosmetic Lasting Effect) | A | C | C |

As is clear from Table 1, the cosmetic composition for the eyes of Examples 1 through 4 had exhibited favorable cosmetic lasting effects. On the other hand, in Comparative Example 1, which does not contain a volatile silicone series oil component even though it contains a film forming agent, and in Comparative Example 2, in which the percentage of the volatile silicone series oil component is low relative to the total amount of the volatile oil component, the cosmetic lasting effects were extremely poor.

In addition, since each of the cosmetic composition for the eyes of Examples 1 through 4 have a moderate hardness, they spread smoothly when utilized, spread easily, are easy to apply and have superior utilization properties. In addition, a silicone series film forming agent is contained within a range from 10.01 to 30% by mass. Therefore, it was possible to realize a cosmetic film strength required of mascara and a supple cosmetic film required for eyeliner.

(Examples of Formulations)

Below, examples of formulations of the cosmetic of the present disclosure will be presented. The present disclosure is not limited by this formulation example at all. Note that the content of each component is indicated as % by mass with respect to the total amount of the product.

Formulation Example 1: Volume Mascara (Components)
(1) light isoparaffin: remainder
(2) dimethyl polysiloxane: 2.0
(3) polyethylene glycol dioleate: 2.0
(4) diglyceryl diisostearate: 2.0
(5) decamethyl cyclopentasiloxane: 30.0
(6) trimethylsiloxysilicic acid: 12.0
(7) polyethylene: 5.0
(8) microcrystalline wax: 3.0
(9) acetic acid DL-α-tocopherol: 0.1
(10) dimethyl distearyl ammonium hectorite: 6.0
(11) purified water: 2.0
(12) 1,3-butylene glycol: 4.0
(13) seaweed extract: 0.1
(14) sodium bicarbonate; 0.2
(15) paraoxybenzoic acid ester: q. s.
(16) sodium dehydroacetate: q. s.
(17) methyl polysiloxane emulsion: q. s.
(18) black iron oxide: 7.0
(Production Method)
A: Heat and dissolve components (1) through (9), then add component (10) to the solution and mix uniformly.
B: Dissolve components (12) through (17) in component (11).
C: Add component (18) to A such that it disperses uniformly.
D: Add B to C and mix.
E: Fill a predetermined container with D to obtain a volume mascara.

Formulation Example 2: Curl Mascara (Component)
(1) light isoparaffin: remainder
(2) dimethyl polysiloxane: 1.0
(3) dimethicone (1.5 CS): 20.0
(4) trimethylsiloxysilicic acid: 12.0
(5) isostearic acid: q. s.
(6) polyethylene glycol dioleate: 2.0
(7) diglyceryl diisostearate: 1.0
(8) N-lauroyl-L-glutamic acid di (phytostearyl.2-octyldodecyl): q. s.
(9) sucrose acetate stearate: 3.0
(10) candelilla wax: 2.0
(11) DL-α-tocopherol acetate: 0.1
(12) dimethyl distearyl ammonium hectorite: 5.0
(13) titanium mica: 2.0
(14) aluminum stearate: q. s.
(15) purified water: 2.0
(16) sodium bicarbonate: 0.1
(17) sodium dehydroacetate: q. s.
(18) seaweed extract: 0.1
(19) black iron oxide: 10.0
(20) ethyl alcohol: 5.0
(21) paraoxybenzoic acid ester: q. s.
(Production Method)
A: Dissolve components (1) to (11), add components (12) to (14) to the solution, and mix uniformly.
B: Dissolve component (15) and components (15) through (18).
C: Add component (19) to A and such that it disperses uniformly.
D: Dissolve component (21) in component (20) and then add the solution to B. Add this to C and mix.
E: Fill a prescribed container with D to obtain curl mascara.

Formulation Example 3: Long Mascara (Components)
(1) light isoparaffin: residue
(2) dimethyl polysiloxane: 3.0
(3) dimethicone (1.5 CS): 20.0
(4) methyl trimethicone: 10.0
(5) trimethylsiloxysilicic acid: 12.0
(6) tri (trimethylsiloxy) silyl propyl carbamic acid pullulan: 3.0
(7) heavy flowing isoparaffin: 4.0
(8) candelilla wax: 3.0
(9) polyethylene: 5.0
(10) acetic acid DL-α-tocopherol: 0.1
(11) dimethyl distearyl ammonium hectorite: 5.0
(12) nylon fibers (1-2 mm): 3.0
(13) polyethylene glycol dioleate: 2.0
(14) diglyceryl diisostearate: 2.0
(15) purified water: 2.0
(16) sodium metaphosphate: q. s.
(17) sodium bicarbonate: 0.1
(18) sodium dehydroacetate: q. s.
(19) 1,3-butylene glycol: 4.0
(20) paraoxybenzoic acid ester: q. s.
(21) methyl polysiloxane emulsion: q. s.
(22) black iron oxide: 7.0
(Production Method)
A: Heat and dissolve components (1) to (10), to which components (11) through (12) are added and dispersed therein. Then add components (13) and (14) and mix uniformly.
B: Dissolve components (14) through (21) in component (15), add component (19) which is heated and dissolved in component (20) to the obtained solution, and mix uniformly.
C: Add ingredient (22) to A, uniformly disperse and mix.
D: Add B to C and mix.
E: Fill predetermined container with D to obtain a long mascara.

Formulation Example 4: Mascara (Components)
(1) light isoparaffin: remainder
(2) methylhydrogen polysiloxane: 1.0
(3) dimethicone (1.5 CS): 20.0
(4) methyl trimethicone: 5.0
(5) castor oil: 2.0
(6) candelilla wax: 3.0
(7) isostearic acid: 3.0
(8) polyethylene: 5.0
(9) microcrystalline wax: 1.0
(10) hexaoxystearic acid dipentaerythritol: 2.0
(11) dextrin palmitate: 13.0
(12) trimethylsiloxysilicic acid: 12.0

(13) tri (trimethylsiloxy) silyl propyl carbamic acid pullulan: 3.0
(14) oleic acid: 1.0
(15) soapberry extract: 0.1
(16) oat extract: 0.1
(17) tetradecene: 0.1
(18) black iron oxide: 6.0
(19) purified water: 2.0
(20) 1,3-butylene glycol: 2.0
(Production Method)
A: Heat and dissolve a portion of part of component (1) and components (2) to (13).
B: Disperse and mix components (14)-(17) in the remainder of component (1).
C: Add B to A and mix.
D: After dissolving component (20) in component (19), add the solution to C and mix.
E: Fill a predetermined container with D to obtain mascara.

Formulation Example 5: Color Mascara (Brown)

(1) light isoparaffin: residue
(2) dimethyl polysiloxane: 1.0
(3) methyl trimethicone: 10.0
(4) decamethyl pentasiloxane: 10.0
(5) trimethylsiloxysilicic acid: 12.0
(6) isostearic acid: q. s
(7) N-lauroyl L-glutamic acid di (phytostearyl.2-octyldodecyl): q. s
(8) polyethylene glycol dioleate: 2.0
(9) diglyceryl diisostearate: 1.0
(10) sucrose acetate stearate; 3.0
(11) candelilla wax: 2.0
(12) acetic acid DL-α-tocopherol: 0.1
(13) dimethyl distearyl ammonium hectorite: 5.0
(14) titanium mica: 2.0
(15) aluminum stearate: q. s
(16) purified water: 15.0
(17) sodium bicarbonate 0.1
(18) sodium dehydroacetate: q. s
(19) seaweed extract: 0.1
(20) black iron oxide: 5.0
(21) red iron oxide: 2.5
(22) ocher: 2.5
(23) ethyl alcohol: 5.0
(24) paraoxybenzoic acid ester: q. s.
(Production Method)
A: Heat and dissolve components (1) through (12), and then add components (13) through (15) to the solution and mix uniformly.
B: Dissolve the component (16) and components (17) through (19).
C: Add components (20) through (22) to A such that they are dispersed uniformly.
D: Add component (24) to component (23) and then add it to B. Add this to C and mix.
E: Fill a predetermined container with D to obtain color mascara.

Formulation Example 6: Combined Mascara and Eyeliner (Components)
(1) light isoparaffin: remainder
(2) methylhydrogen polysiloxane: 1.0
(3) dimethicone (1.5 CS): 18.0
(4) methyl trimethicone: 5.0
(5) castor oil: 2.0
(6) candelilla wax: 5.0
(7) isostearic acid: 3.0
(8) polyethylene: 5.0
(9) microcrystalline wax: 5.0
(10) glyceryl tri-2-ethylhexanoate: 2.0
(11) dextrin palmitate: 13.0
(12) trimethylsiloxysilicic acid: 12.0
(13) tri (trimethylsiloxy) silyl propyl carbamic acid pullulan: 3.0
(14) oleic acid: 1.0
(15) soapberry extract: 0.1
(16) oat extract: 0.1
(17) tetradecene: 0.1
(18) black iron oxide: 6.0
(19) purified water: 2.0
(20) 1,3-butylene glycol: 2.0
(Production Method)
A: Heat and dissolve a portion of component (1) and components (2) through (13).
B: Disperse and mix components (14) through (17) in the remainder of component (1).
C: Add B to A and mix.
D: After dissolving component (20) in component (19), add the solution to C and mix.
E: A predetermined container was filled with D to obtain a cosmetic for the eyes which may be employed as both mascara and eyeliner.

Formulation Example 7: Mascara and Eye Liner (Brown)

(Components)
(1) light isoparaffin: remainder
(2) methylhydrogen polysiloxane: 1.0
(3) dimethicone (1.5 CS): 18.0
(4) methyl trimethicone: 5.0
(5) castor oil: 2.0
(6) candelilla wax: 5.0
(7) isostearic acid: 3.0
(8) glyceryl tri-2-ethylhexanoate: 2.0
(9) polyethylene: 5.0
(10) microcrystalline wax: 5.0
(11) trimethylsiloxysilicic acid: 15.0
(12) dextrin palmitate: 13.0
(13) oleic acid: 1.0
(14) soapberry extract: 0.1
(15) oat extract: 0.1
(16) tetradecene: 0.1
(17) black iron oxide: 3.0
(18) red iron oxide: 1.0
(19) ocher: 1.0
(20) purified water: 2.0
(21) 1,3-Butylene glycol: 2.0
(Production Method)
A: Heat and dissolve a portion of component (1) and components (2) through (12).
B: Disperse and mix components (13) to (19) in the remainder of component (1).
C: Add B to A and mix.
D: After dissolving component (21) in component (20), add the solution to C and mix.
E: Fill a prescribed container with D to obtain a cosmetic for the eyes which may be employed as both mascara and eyeliner.

The invention claimed is:

1. A cosmetic composition for the eyes, comprising:
   10.01 to 30% by mass of a silicone series film forming agent; and
   25 to 70% by mass of a volatile oil component with respect to the total amount of the cosmetic composition for the eyes;
   an amount of a volatile silicone series oil component being 25% by mass or greater with respect to the total volatile oil component; and
   the hardness being 30 or greater and 100 or less,
   wherein the silicone series film forming agent is one of trimethylsiloxysilicic acid and siliconeized pullulan.

2. A cosmetic composition for the eyes as defined in claim 1, wherein:
   the volatile silicone series oil component is a volatile straight chain silicone series oil component.

3. A cosmetic composition for the eyes as defined in claim 1, further comprising:
   0.01 to 20% by mass of a solid oil component.

4. A cosmetic composition for the eyes as defined in claim 1, further comprising purified water in an amount within a range from 0.01 to 5% by mass.

5. A cosmetic composition for the eyes as defined in claim 1, further comprising:
   red iron oxide.

6. A cosmetic composition for the eyes as defined in claim 1, wherein:
   the cosmetic composition for the eyes is mascara.

7. A cosmetic composition for the eyes as defined in claim 1, wherein:
   the cosmetic composition for the eyes is capable of being utilized as both mascara and eyeliner.

8. A cosmetic composition for the eyes as defined in claim 1, wherein:
   the siliconeized pullulan is tri (trimethylsiloxy) silylpropylcarbamic acid pullulan.

9. A cosmetic composition for the eyes as defined in claim 8, wherein:
   the volatile silicone series oil component is a volatile straight chain silicone series oil component.

* * * * *